(12) United States Patent
Fujita (10) Patent No.: US 8,556,790 B2
(45) Date of Patent: Oct. 15, 2013

(54) FLAP FOLDING SYSTEM FOR DISPOSABLE ARTICLE TO BE WORN

(75) Inventor: Yukihiko Fujita, Osaka (JP)

(73) Assignee: Zuiko Corporation, Osaka (JP)

( * ) Notice: Subject to any disclaimer, the term of this patent is extended or adjusted under 35 U.S.C. 154(b) by 167 days.

(21) Appl. No.: 13/255,569

(22) PCT Filed: Apr. 14, 2010

(86) PCT No.: PCT/JP2010/056651
§ 371 (c)(1),
(2), (4) Date: Sep. 9, 2011

(87) PCT Pub. No.: WO2010/119884
PCT Pub. Date: Oct. 21, 2010

(65) Prior Publication Data
US 2011/0319243 A1    Dec. 29, 2011

(30) Foreign Application Priority Data

Apr. 17, 2009   (JP) ................................ 2009-100871

(51) Int. Cl.
*B65H 45/28*   (2006.01)

(52) U.S. Cl.
USPC ............ 493/357; 493/437; 493/359; 493/454

(58) Field of Classification Search
USPC ......... 493/357, 359, 360, 436, 437, 442, 454, 493/450
See application file for complete search history.

(56) References Cited

U.S. PATENT DOCUMENTS 5,779,831 A     7/1998  Schmitz
7,322,925 B2 *  1/2008  Couillard et al. ............. 493/450

2002/0002358 A1     1/2002  Durrance et al.
2002/0003022 A1     1/2002  Csida et al.
2013/0029827 A1 *   1/2013  Fujita ........................... 493/405

FOREIGN PATENT DOCUMENTS

| JP | 07-205943 A | 8/1995 |
| JP | 09-301329 A | 11/1997 |
| JP | 2002-087695 A | 3/2002 |
| JP | 2003-102777 A | 4/2003 |
| WO | 2007/070113 A1 | 6/2007 |

OTHER PUBLICATIONS

International Search Report for corresponding International Application No. PCT/JP2010/056651 mailed Jul. 20, 2010.

* cited by examiner

*Primary Examiner* — Alexandra Elve
*Assistant Examiner* — Adam Moon
(74) *Attorney, Agent, or Firm* — Renner, Otto, Boisselle & Sklar, LLP

(57) ABSTRACT

A flap folding system for a disposable article, includes: main pads each for receiving a main body on a main holding surface thereof provided along a conveyance circle about a main rotation shaft and moving along the conveyance circle following rotation of the main rotation shaft while holding the main body on the main holding surface; a pair of side pads provided for each main pad adjacent to the conveyance circle of the main pad each for receiving an end portion of the flap in a girth direction on a sub-holding surface thereof provided along the conveyance circle and holding the end portion of the flap on the sub-holding surface; and a folding mechanism for rotating the side pads with respect to the main pad so that the sub-holding surfaces of the side pads oppose the main holding surface of the main pad, thereby folding the flap.

7 Claims, 11 Drawing Sheets

FIG.11B

FLAP FOLDING SYSTEM FOR DISPOSABLE ARTICLE TO BE WORN

TECHNICAL FIELD

The present invention relates to a folding system for side flaps of disposable worn articles.

BACKGROUND ART

Folding systems for folding disposable worn articles have been proposed in the art (see the first to third patent documents below). For example, in the second patent document, end portions of an article are folded by swing arms adjacent to a member for holding the article. However, the swing arms only swing so as to lift up end portions of articles, and if pliant portions such as flaps of worn articles are attempted to fold with such a folding device, variations may occur in the fastening positions.

CITATION LIST

Patent Document

[FIRST PATENT DOCUMENT] Japanese Laid-Open Patent Publication No. 2003-102777 (Abstract)
[SECOND PATENT DOCUMENT] Japanese Laid-Open Patent Publication No. 2002-87695 (Abstract)
[THIRD PATENT DOCUMENT] Japanese Laid-Open Patent Publication No. 7-205943 (Abstract)

SUMMARY OF INVENTION

Technical Problem

However, with a conventional folding system, it is not possible to accurately fold wide, soft portions such as side flaps of worn articles.

It is therefore an object of the present invention to provide a folding system capable of accurately folding side flaps of a disposable worn article.

Solution to Problem

In order to achieve the object set forth above, a flap folding system of the present invention is a device for folding a flap of a worn article having: a main body including a back portion covering a rear torso of a wearer, a crotch portion covering a crotch of the wearer, and a front portion covering a front torso of the wearer; and a flap extending in a girth direction from an edge portion of one of the back portion and the front portion of the main body to be fastened to the other one of the back portion and the front portion, the folding system comprising: a main rotation shaft; a plurality of main pads each for receiving at least the main body on a main holding surface thereof provided along a (virtual) conveyance circle about the main rotation shaft and moving along the conveyance circle following rotation of the main rotation shaft while holding the main body on the main holding surface; a pair of side pads provided for each of the main pads adjacent to each of the main pads on the conveyance circle for receiving at least an end portion of the flap in the girth direction on sub-holding surfaces thereof provided along the conveyance circle and holding the end portion of the flap on the sub-holding surfaces; and a folding mechanism for rotating the pair of side pads with respect to each of the main pads so that the sub-holding surfaces of the pair of side pads oppose the main holding surface of each of the main pads, thereby folding the flap.

Advantageous Effects of Invention

With the present invention, flaps are folded while end portions of the flaps are held by the holding surfaces, it is possible to accurately fold wide, soft flaps.

DESCRIPTION OF EMBODIMENTS

It is preferred in the present invention that the folding mechanism rotates the pair of side pads with respect to the main pad to a position such that the sub-holding surfaces oppose the main holding surface and the sub-holding surfaces are parallel to the main holding surface.

In this aspect, the rotation is done to a position (the squarely-opposing position) where the sub-holding surfaces oppose, and are parallel to, the main holding surface, i.e., the sub-holding surfaces squarely oppose the main holding surface, thereby allowing for more accurate folding of flaps.

It is preferred in the present invention that the folding mechanism includes: arms rotating about a pair of first axes parallel to the main rotation shaft; wrists rotatably supporting the side pads about a pair of second axes parallel to the first axes at a tip of the arms; and a driving mechanism for rotating the arms and the wrists in a predetermined rotation direction so as to fold the flap.

In this aspect, the side pad is rotatably supported via both the arm and the wrist, thereby allowing the sub-holding surface of the side pad to be squarely facing the main holding surface.

It is preferred in the present invention that the driving mechanism includes: an arm rotating mechanism for rotating the arm about the first axis so that the side pad moves from a first position adjacent to the main pad to a second position on an outer (circumferential) side of the main pad as the main pad rotates along the conveyance circle following the rotation of the main rotation shaft; and a wrist rotating mechanism for rotating the side pad about the second axis at the wrist following the rotation of the arm by the arm rotating mechanism.

In this aspect, the side pad rotates about the wrist while revolving together with the arm, and smooth folding can therefore be expected.

It is preferred in the present invention that the main pad and the side pads pick up a laminated web to be the worn article at a pickup position upstream of a folding position where the folding is done, and the main pad hands over the laminated web to a conveyer device downstream at a hand-over position downstream of the folding position.

It is preferred in the present invention that the folding system further includes a severing device for severing the laminated web being stretched along the conveyance circle by the main pad and the side pads at a severing position between the pickup position and the folding position.

In this aspect, the web is held in a stretched state, thereby allowing for accurate severing.

It is preferred in the present invention that the holding of the main body by the main pad is done at least in an area of the main pad where the side pads oppose the main pad.

In this aspect, fastening is done in a state where the main body to which the flap is fastened is held and the flap is also held, thereby allowing for accurate fastening.

In the present invention, a first fastener member may be provided on a skin-contact surface side of the flap to be folded, and a second fastener member may be provided on the main body on which the folded flap lies so as to engage with the first fastener member.

In the present invention, the main pads, the pairs of side pads and the folding mechanisms may be arranged in two rows along the conveyance circle, with the main pads of the two rows arranged in a staggered pattern with each other.

In this aspect, two rows of worn articles arranged in a staggered pattern obtained by severing a single web in a generally S-shaped pattern can be folded in parallel.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

[Embodiment 1]

Embodiment 1 of the present invention will now be described with reference to the drawings.

FIGS. 1 to 8 show Embodiment 1.

Figure 10:
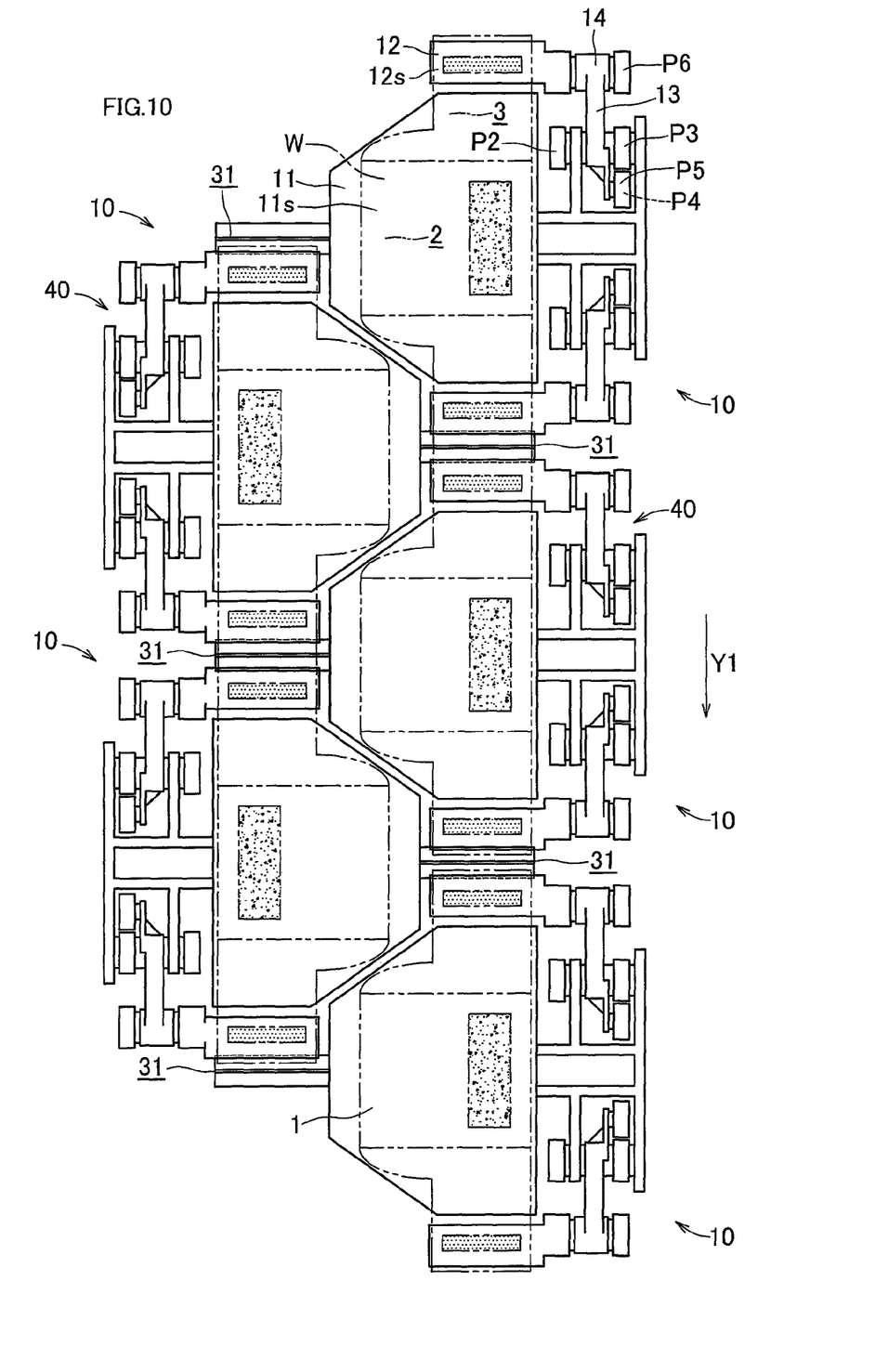
FIG. 10 is a schematic plan view showing an arrangement of main pads, side pads and anvils of the folding system in a case where diapers are arranged in two rows.

Diaper 1:

As shown in FIG. 10, a diaper 1 of Embodiment 1 includes a diaper body 2, and a pair of flaps 3. The diaper body 2 includes a front portion 20 covering the front torso of the wearer, a back portion 21 covering the rear torso of the wearer, and a crotch portion 22 covering the crotch between the front portion 20 and the back portion 21.

Figure 1A:
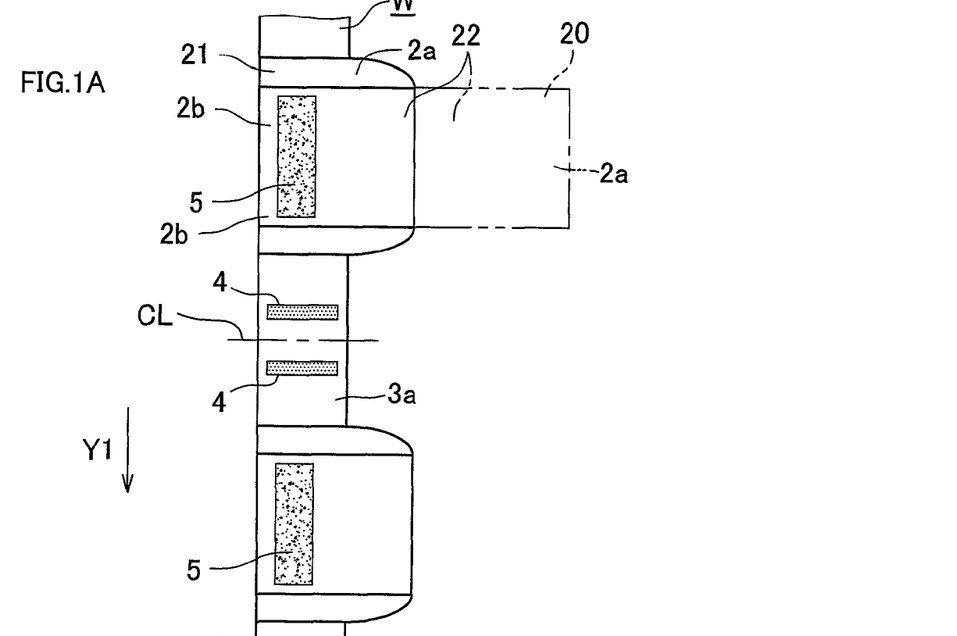
FIGS. 1A, 1B and 1C are schematic plan views each showing a step of manufacturing a diaper produced by a folding system according to Embodiment 1 of the present invention.
Figure 1B:
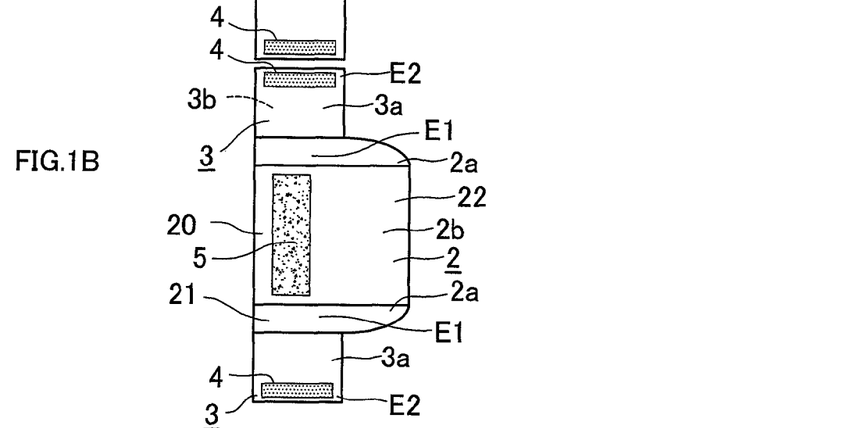

As shown in FIG. 1B, each flap 3 extends out from an edge portion E1 of the diaper body 2 in a girth direction Y.

A first fastener member formed by a male touch fastener 4 is fixed to a skin-contact surface side 3a of an end portion E2 of each flap 3 in the girth direction Y.

Figure 1C:
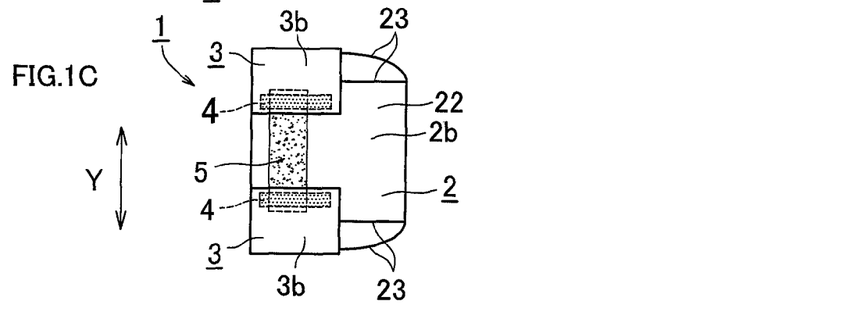

On the other hand, a second fastener member formed by a female touch fastener 5 is provided on a non-skin-contact surface 2b of the front portion 20. As shown in FIG. 1C, the male touch fasteners 4 engage with the female touch fastener 5.

Note that where the non-skin-contact surface 2b of the diaper body 2 is formed by a non-woven fabric, the second fastener member may be formed by the non-woven fabric.

The term "skin-contact surface side" as used herein refers to the side which faces the skin surface of the wearer when the diaper 1 is worn, and the "non-skin-contact surface side" refers to the side opposite to the skin-contact surface side.

An adsorbent body (not shown) is provided on the diaper body 2.

Three-dimensional gathers may be provided on the diaper body 2.

The diaper body 2 may include around-leg portions 23 which have been cut so as to conform to the legs of the wearer. Elastic members formed by rubber threads, or the like, for example, may be provided so as to conform to the legs of the wearer in the around-leg portion 23 or portions of the flaps 3 that are connected to the around-leg portions 23.

Moreover, an elastic member for fitting the diaper 1 to the wearer may be provided in portions of the front portion 20 and the back portion 21 of the diaper body 2 which are to be present around the torso and in the flaps. The elastic member may be, for example, a plurality of rubber threads or rubber tapes, a material including a film or a thermoplastic resin, or the like.

A laminated web W to be the diaper 1 is folded in two in the crotch portion 22 as shown in FIG. 1A, and is folded so that a skin-contact surface 2a of the back portion 21 and the skin-contact surface 2a of the front portion 20 indicated by a two-dot-chain line lie on each other. As shown in FIG. 10, the skin-contact surface side 3a (FIG. 1B) of the flap 3 is folded toward the female touch fastener 5 of the front portion 20 of the diaper body 2, and the diaper 1 is shipped with the set of fasteners 4 and 5 engaged with each other and the pair of flaps 3 tentatively attached to the diaper body 2.

When wearing the diaper 1, a wearer puts it on as if it were a pants-type diaper, with the flaps 3 tentatively attached to the diaper body 2. On the other hand, if the diaper 1 does not sufficiently fit to the wearer, the male touch fasteners 4 of the flaps 3 may be once taken off the female touch fastener 5 of the diaper body 2, and the male touch fasteners 4 may be re-attached to the female touch fastener 5, thereby fitting the diaper 1 to the wearer.

Folding System:

Next, a folding system for severing the diaper 1 and folding the flaps 3 as shown in FIGS. 1A to 1C will be described.

Figure 2:
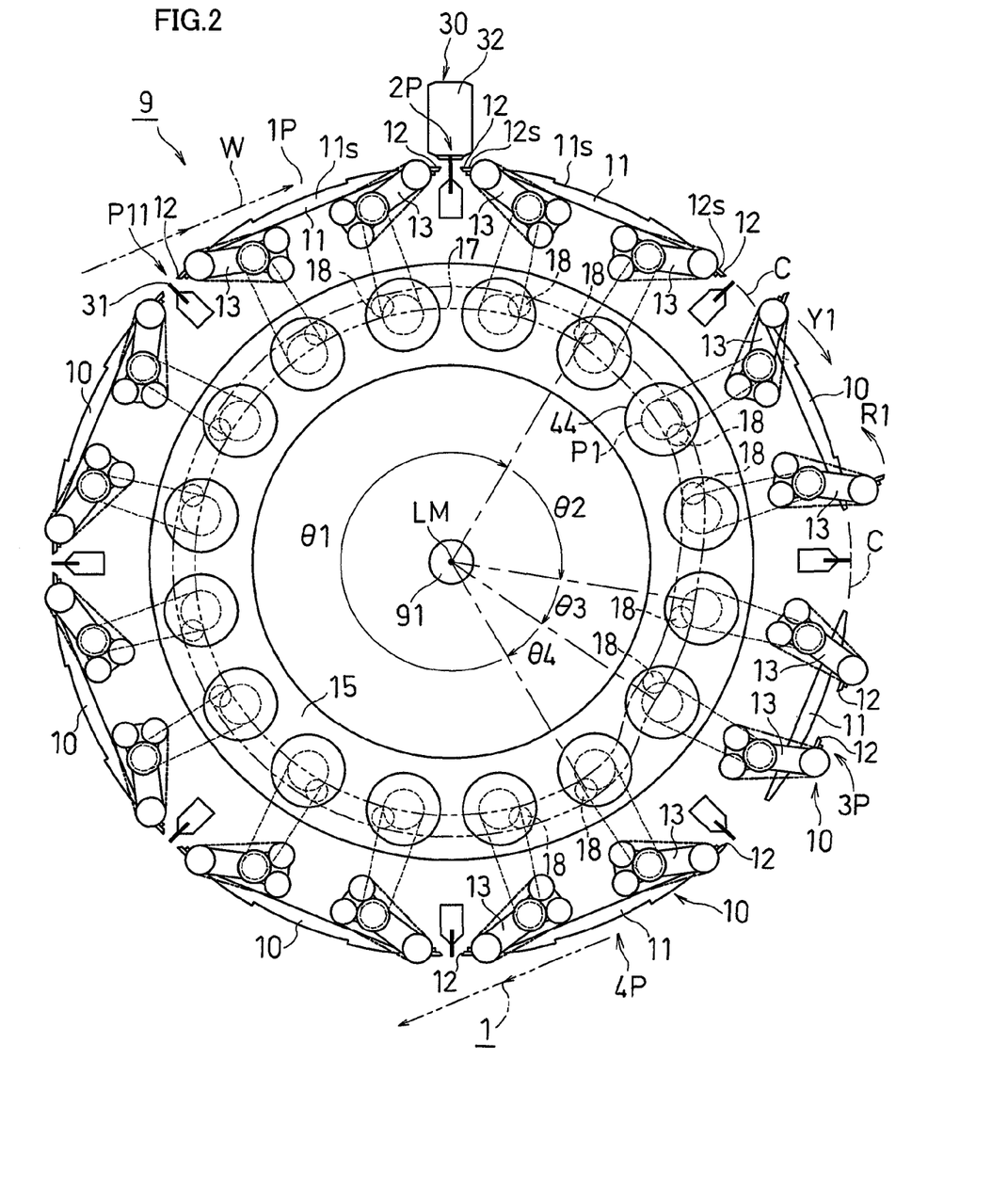
FIG. 2 is a schematic front view of the folding system.

As shown in FIG. 2, this folding system includes a folding drum 9. A cutter roller 32 is arranged so as to oppose the folding drum 9.

The folding drum 9 includes a plurality of folding units 10 rotating about a main rotation shaft 91. The folding drum 9 includes a fixed frame 15 for rotatably supporting the main rotation shaft 91 of FIG. 7, and a rotating frame 16 rotatably supported about the fixed frame 15. A torque from a motor (not shown) is input to the main rotation shaft 91, and the rotating frame 16 rotates about the main axis LM following the rotation of the main rotation shaft 91.

Figure 6A:
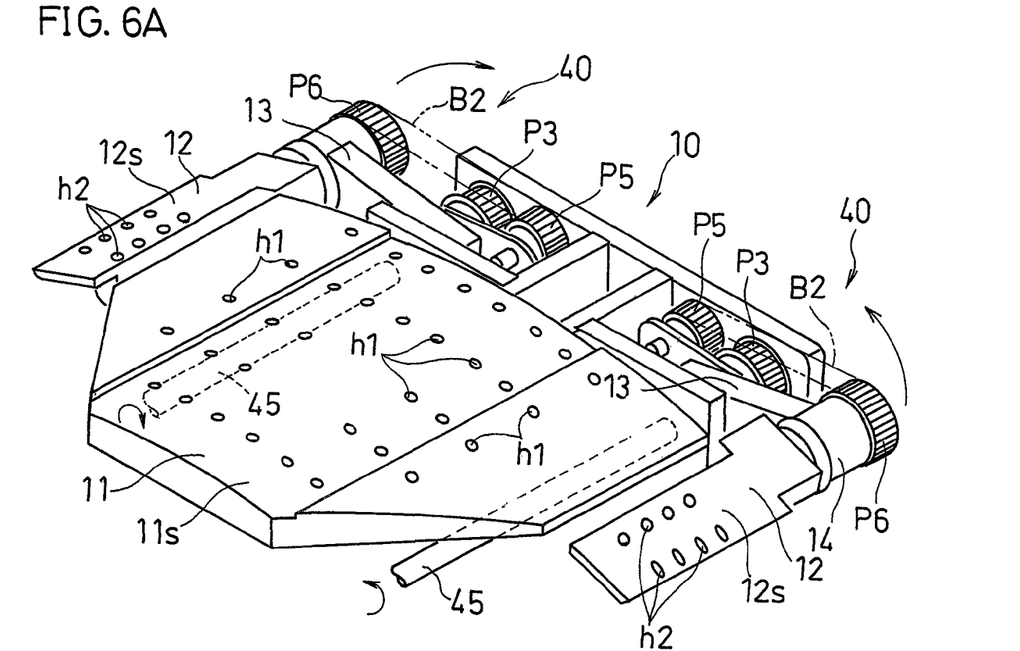
FIGS. 6A and 6B are schematic perspective views each showing a main pad and side pads of the folding system.
Figure 6B:
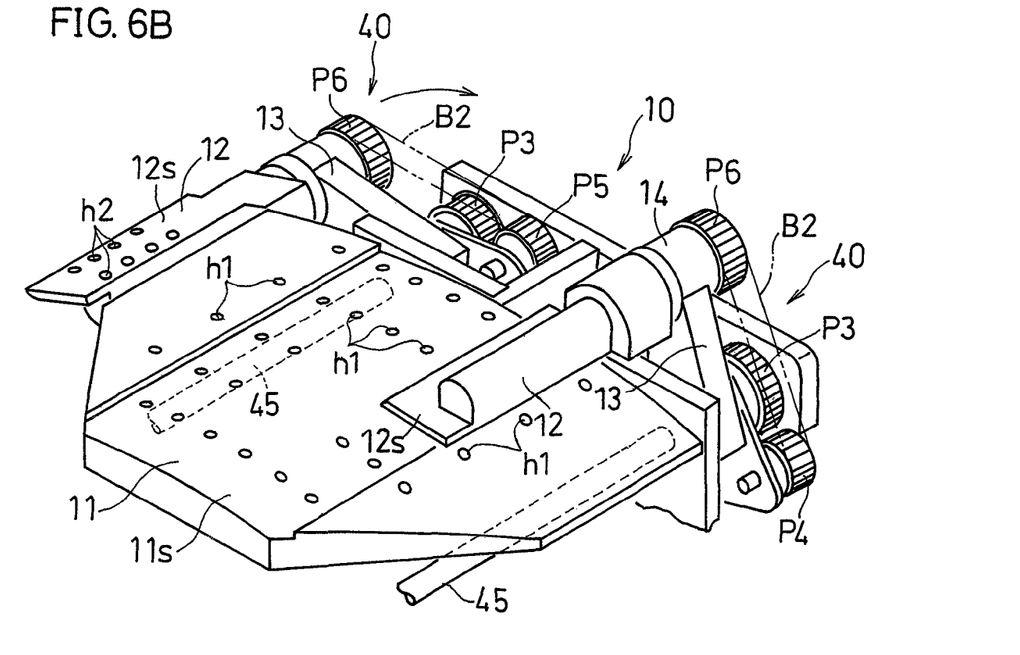

As shown in FIGS. 6A and 6B, each folding unit 10 includes an anvil 31 (FIG. 3), a main pad 11, a pair of side pads 12, and a pair of folding mechanisms 40.

Figure 7:
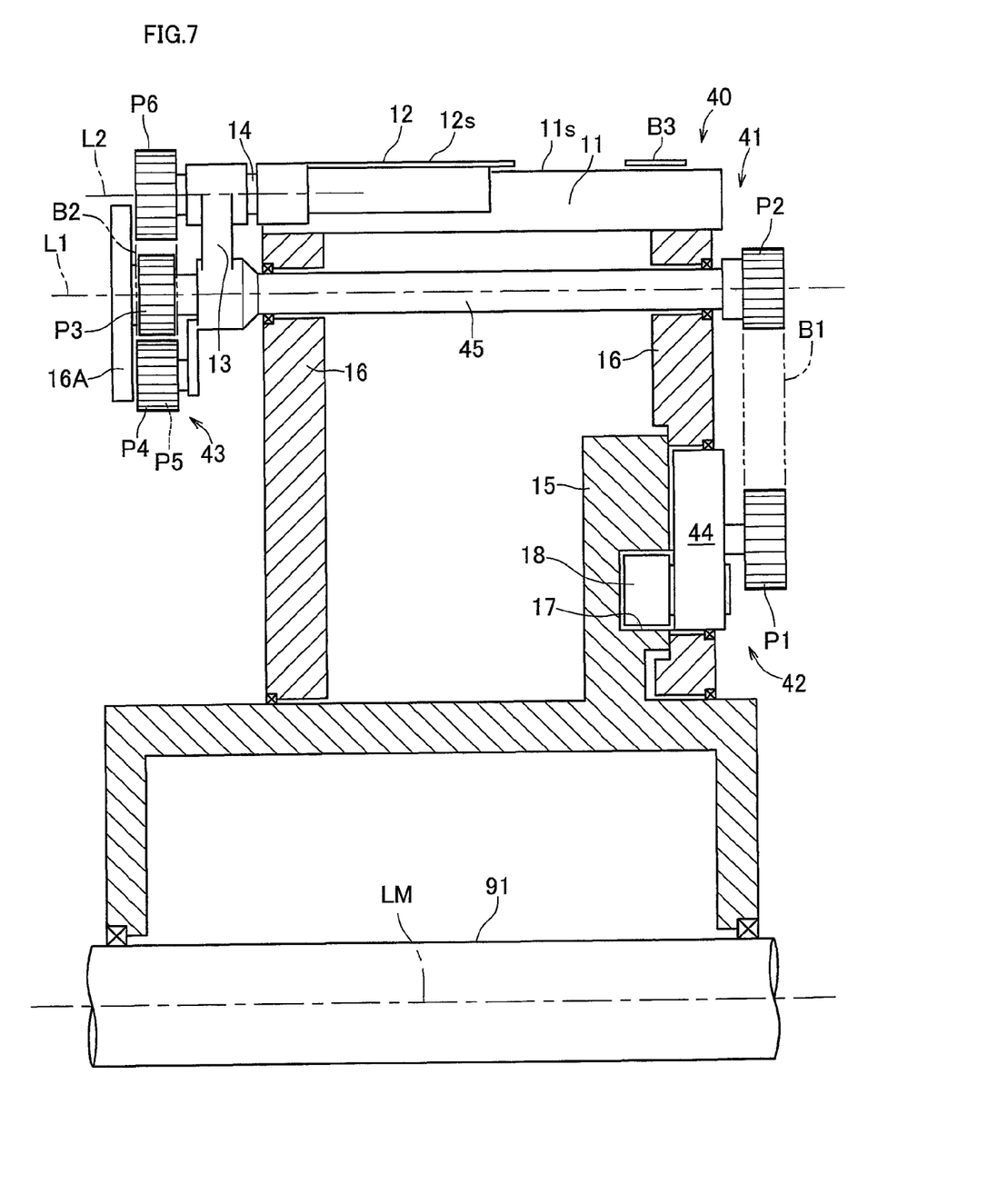
FIG. 7 is a schematic cross-sectional view showing a driving mechanism of the folding system.

Each folding unit 10 including the anvil 31 (FIG. 3), the main pad 11, the side pads 12 and the folding mechanisms 40 is attached to the rotating frame 16 shown in FIG. 7, and rotates about the main axis LM together with the rotating frame 16 following the rotation of the main rotation shaft 91.

Figure 4:
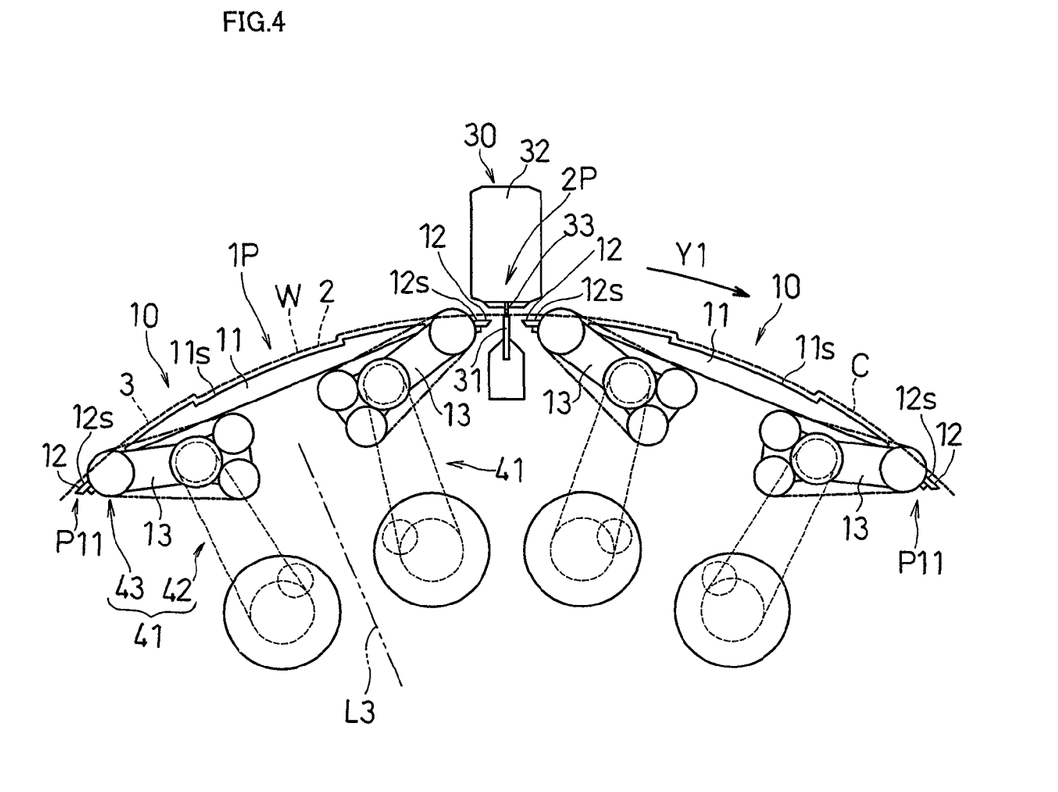
FIG. 4 is a schematic front view showing a portion in the vicinity of a severing position in the folding system.

As shown in FIG. 4, the anvil 31 forms a severing device 30 together with the cutter roller 32 and a blade 33.

The severing device 30 severs the web W into individual diapers downstream of the pickup position 1P of the web W.

In this folding system, the main pad 11 and the side pads 12 of FIG. 2 pick up the web W to be the diaper 1 at the pickup position 1P upstream of the folding position 3P where the folding is done. The main pad 11 hands over the diaper 1 to a conveyer device (not shown) at the hand-over position 4P downstream of the folding position 3P. The folding position 3P is located downstream of the severing position 2P.

The main pad 11 receives at least the main body 2 on a main holding surface 11s which is provided along the conveyance circle C (FIG. 5C) about the main rotation shaft 91. Then, the main pad 11 moves along the conveyance circle C following the rotation of the main rotation shaft 91 while holding the main body 2 on the main holding surface 11s. As shown in FIG. 6A, a plurality of air holes h1 are open on the main holding surface 11s for holding the main body 2 through suction by a negative pressure, for example.

For each main pad 11, a pair of side pads 12 are arranged adjacent to the main pad 11 on the conveyance circle C (FIG. 5C) of the main pad 11. The side pads 12 receive at least the end portions E2 of the flaps 3 in the girth direction Y of FIG. 3 on the sub-holding surfaces 12s which are provided along the conveyance circle C (FIG. 5C). Then, the end portions E2 of the flaps 3 are held on the sub-holding surfaces 12s. A plurality of air holes h2 of FIG. 6A are open in the sub-holding surface 12s for holding the flaps 3 through suction by a negative pressure, for example.

Figure 8:
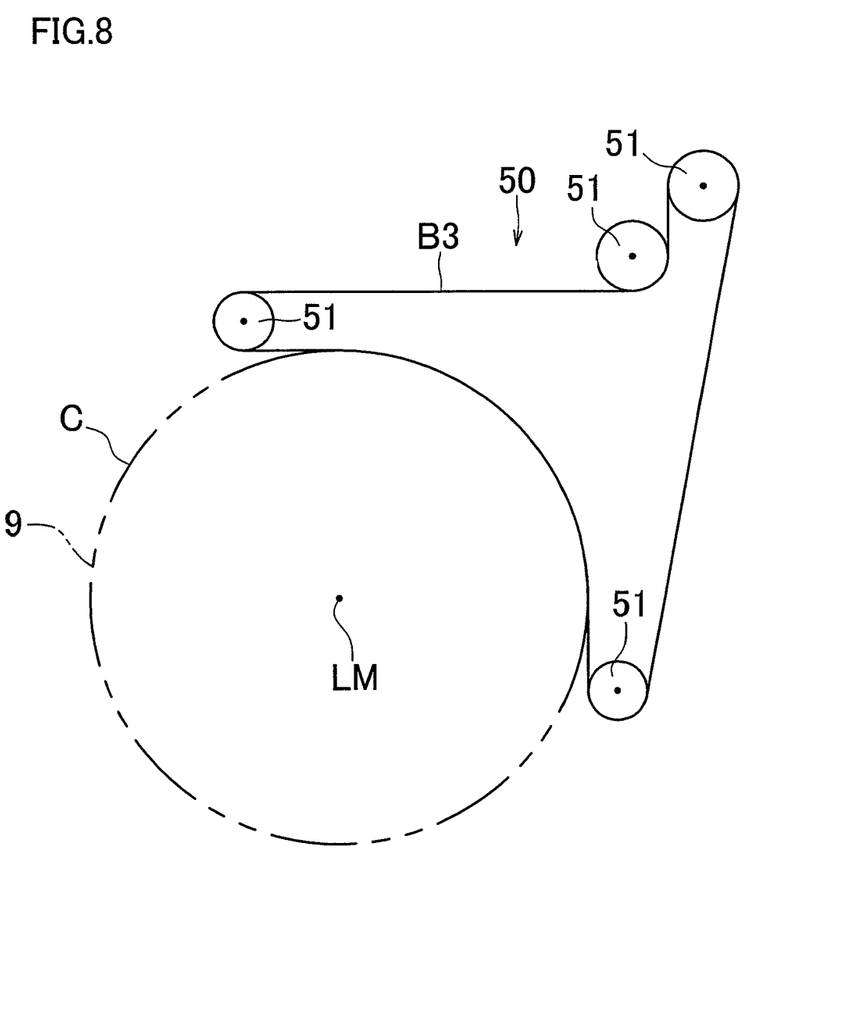
FIG. 8 is a schematic front view showing a pressing mechanism of the folding system.

FIG. 8 shows a pressing mechanism 50.

The pressing mechanism 50 includes an endless third belt B3 wound around a plurality of rollers 51. The third belt B3 presses an area of the diaper body 2 of FIG. 1A where the flaps 3 are not lying thereon on the folding drum 9. Thus, the two-folded area of the diaper body 2 that cannot be held by the suction of the main holding surface 11s is pressed from the outer (circumferential) side of the folding drum 9.

The folding mechanism 40 of FIG. 4 rotates the pair of side pads 12 with respect to the main pad 11 so that the sub-holding surfaces 12s of the pair of side pads 12 oppose the main holding surface 11s of the main pad 11 as shown in FIG. 5C, thereby folding the flaps 3.

The folding mechanism 40 will now be described.

Figure 5A:
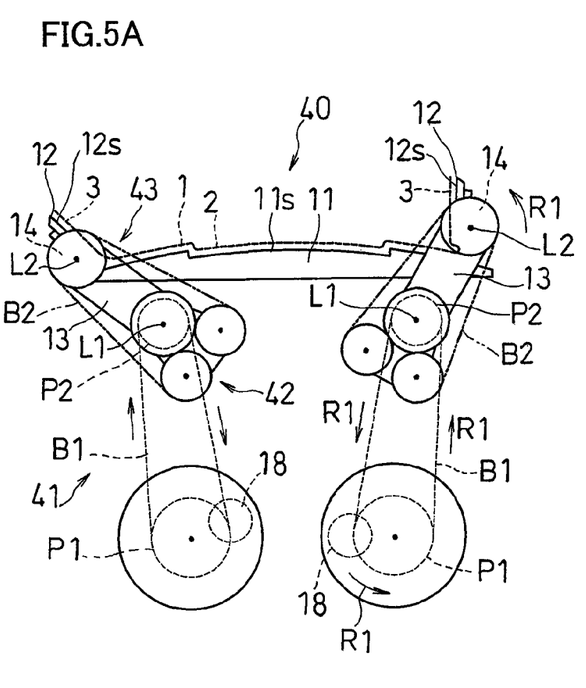
FIGS. 5A, 5B and 5C are schematic front views each showing a driving mechanism of the folding system.
Figure 5B:
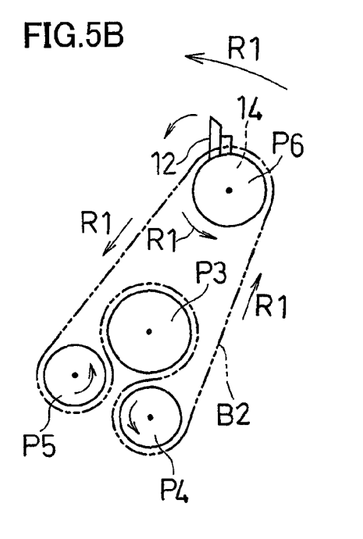
Figure 5C:
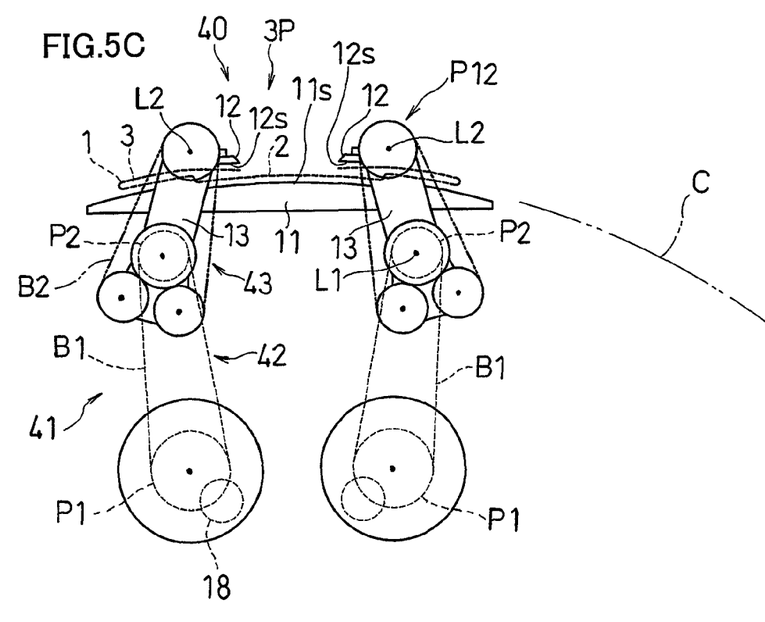

As shown in FIGS. 4, 5A and 5C, the folding mechanism 40 rotates the pair of side pads 12 with respect to the main pad 11 to a position such that the sub-holding surfaces 12s oppose the main holding surface 11s and the sub-holding surfaces 12s are parallel to the main holding surface 11s. Each folding mechanism 40 includes an arm 13, a wrist 14, and a driving mechanism 41.

The arm 13 of FIG. 7 rotates about one of a pair of first axes L1 parallel to the main rotation shaft 91. At the tip of each arm 13, the wrist 14 rotatably supports the side pad 12 about one of a pair of second axes L2. The second axes L2 are parallel to the first axes L1. The driving mechanism 41 of FIG. 4 rotates the arm 13 and the wrist 14 in a predetermined rotation direction so as to fold the flap 3.

In FIG. 4, the driving mechanism 41 includes a pair of arm rotating mechanisms 42 and a pair of wrist rotating mechanisms 43. Each folding unit 10 has a left-right symmetric structure about the normal L3 of the drum. One arm rotating mechanism 42 and one wrist rotating mechanism 43 will now be described.

As each main pad 11 rotates along the conveyance circle C following the rotation of the main rotation shaft 91 (FIG. 2), the arm rotating mechanism 42 rotates the arm 13 about the first axis L1 so that the side pad 12 moves from the first position P11 adjacent to the main pad 11 of FIG. 4 to the second position P12 on the outer (circumferential) side of the main pad 11 of FIG. 5C.

On the other hand, the wrist rotating mechanism 43 rotates the side pad 12 about the second axis L2 at the wrist 14 following the rotation of the arm 13 by the arm rotating mechanism 42. With the rotation of the wrist 14 and the rotation of the arm 13, the side pad 12 rotates to the second position P12 and the sub-holding surface 12s rotates to oppose the main holding surface 11s, thereby folding the flap 3, as shown in FIG. 5C.

The air holes h1 of the main pad 11 are provided at least in portions where the sub-holding surfaces 12s of the side pads 12 oppose the main pad 11 or areas in the vicinity thereof. Therefore, it is possible to hold not only the flaps 3 but also the diaper body 2 even during the folding process.

Next, the details of the structure of the arm rotating mechanism 42 will be described.

As indicated by a two-dot-chain line of FIG. 2, a circumferential cam groove 17 is formed in the fixed frame 15. On the other hand, a rotating member 44 is rotatably supported by the rotating frame 16 of FIG. 7 for each arm rotating mechanism 42. A cam follower 18 is attached to the rotating member 44 at a position that is eccentric with respect to the rotating member 44. A first pulley P1 is attached coaxially to the rotating member 44.

The rotating member 44 rotates about the main rotation shaft 91 together with the rotating frame 16 while the rotating member 44 swings as the cam follower 18 of FIG. 2 is guided along the cam groove 17, thereby making the first pulley P1 reciprocally rotate together with the rotating member 44.

An arm rotation shaft 45 is rotatably attached to the rotating frame 16. A second pulley P2 and the arm 13 are attached respectively to one end and the other end of the arm rotation shaft 45. As the first pulley P1 reciprocally rotates, the arm 13 swings via an endless first belt B1, the second pulley P2 and the arm rotation shaft 45, thereby making the side pad 12 reciprocate between the first position P11 of FIG. 4 and the second position P12 of FIG. 5C.

Next, the details of the structure of the wrist rotating mechanism 43 will be described.

A third pulley P3 is provided coaxially with the arm rotation shaft 45 on the other end of the arm rotation shaft 45 of FIG. 7. The third pulley P3 is fixed to a rotating frame 16A so as not to rotate.

As shown in FIGS. 5A and 5B, fourth to sixth pulleys P4 to P6 are arranged around the third pulley P3. An endless second belt B2 is wound around these pulleys P3 to P6. The sixth pulley P6 of FIG. 7 is fixed to one end of the rotation shaft forming the wrist 14. The side pad 12 is fixed to the other end of the wrist 14.

Now, if the first pulley P1 of FIG. 5A rotates in the closing direction R1, the first belt B1 also rotates in the closing direction R1, thereby making the second pulley P2 and the arm 13 rotate in the closing direction R1. On the other hand, since the third pulley P3 of FIG. 5B does not rotate, the second belt B2 rotates in the closing direction R1 following the rotation of the arm 13 of FIG. 5A, and the sixth pulley P6 of FIG. 5B rotates in the closing direction R1. Thus, the side pad 12 rotates in the closing direction R1 together with the wrist 14.

Therefore, the wrist 14 rotates in the closing direction R1 following the rotation of the arm 13 of FIG. 5A in the closing direction R1. Thus, as shown in FIG. 5C, as the arm 13 rotates in the closing direction R1, the side pad 12 rotates about the first axis L1 while rotating about the second axis L2. The side pad 12 rotates to an attitude such that the sub-holding surface 12s is parallel to the main holding surface 11s, so that the sub-holding surface 12s opposes the main holding surface 11s.

Thus, by the rotation, the flaps 3 of the diaper 1 of FIG. 1B are folded as shown in FIG. 10.

Note that the action by which the side pad 12 of FIG. 5C returns from the second position P12 back to the first position P11 as shown in FIG. 4 (the opening action) is reverse from the rotation action in the closing direction R1, and will not be further described below.

Next, the operation of producing diapers 1 from the web W will be described.

As shown in FIG. 1A, the web W in which the diaper bodies 2 are folded in two is supplied, in the form of a continuous member, onto the folding drum 9 at the pickup position 1P of FIG. 2.

Figure 3:
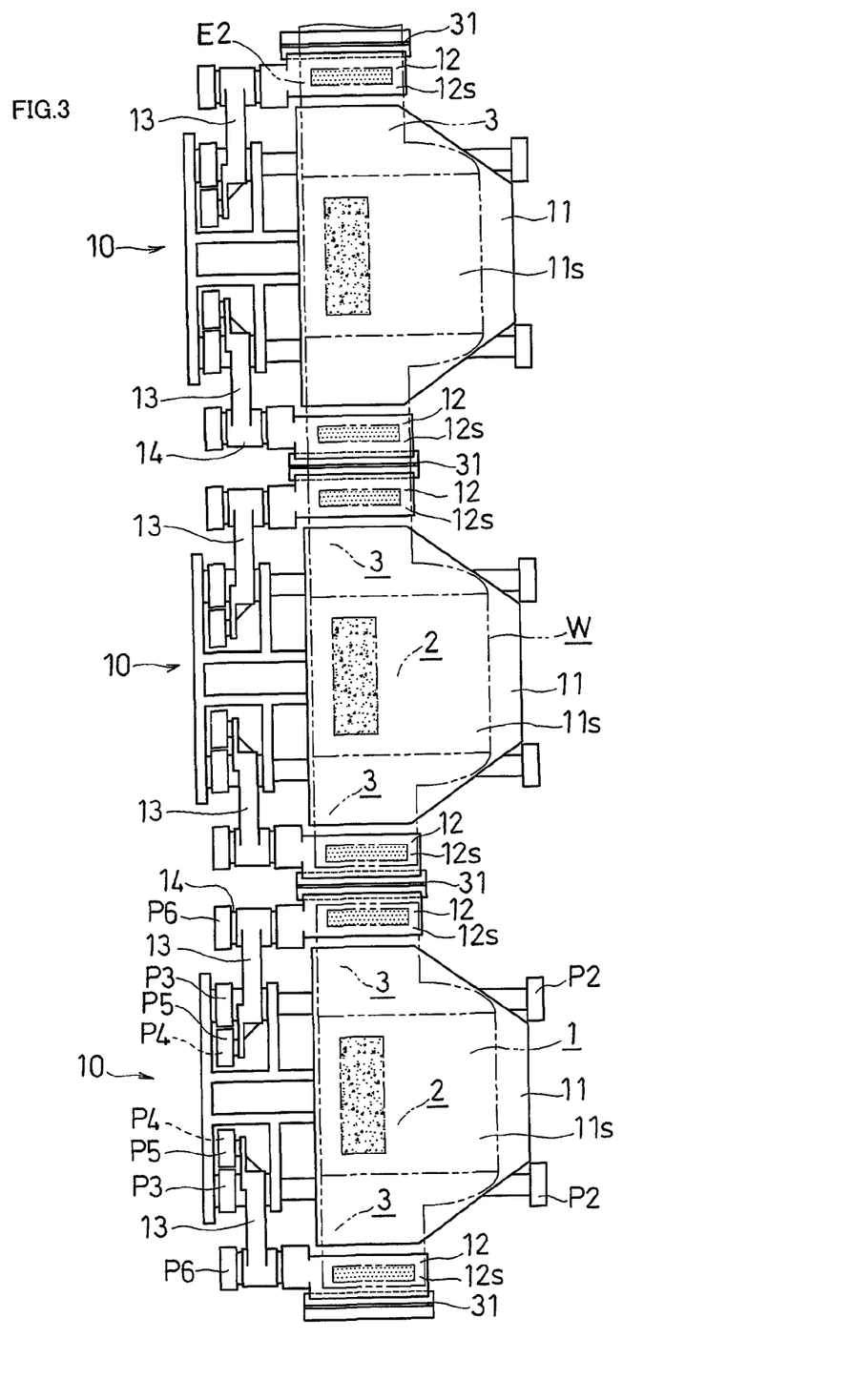
FIG. 3 is a schematic plan view of the folding system.

In the angle θ1 including the pickup position 1P, the side pads 12 are in the open, first position P11. Therefore, the main holding surface 11s and the sub-holding surfaces 12s shown in FIG. 3 receive the web W by sucking and holding the web W. In this process, the diaper body 2 is placed on the main holding surface 11s with the flaps 3 bridging between the main holding surface 11s and the sub-holding surfaces 12s, as shown in FIG. 3, thus holding the web W on these surfaces 11s and 12s.

Note that through the angle θ1 of FIG. 1, the diameter of the cam groove 17 is constant.

As the folding drum 9 of FIG. 2 rotates in this state, the web W being stretched along the conveyance circle C by the main pad 11 and the side pads 12 is severed along the severing line CL of FIG. 1A at the severing position 2P between the pickup position 1P and the folding position 3P into individual diapers 1 as shown in FIG. 1B.

The severed diaper 1 is folded as follows at the folding position 3P of FIG. 2.

In the angle θ2 about the main rotation shaft 91, the diameter of the cam groove 17 gradually decreases as it extends downstream Y1. Through the angle θ2, as the folding unit 10 rotates downstream Y1, the arms 13 and the wrists 14 rotate in the closing direction R1 (FIG. 5A).

That is, as the folding unit 10 rotates toward the folding position 3P, the cam follower 18 is guided along the cam groove 17 so that the arm 13 rotates in the closing direction R1 and the wrist 14 of FIG. 5A rotates in the closing direction R1 as described above. As the arms 13 and the wrists 14 rotate so that the sub-holding surfaces 12s squarely oppose the main holding surface 11s as indicated by the folding position 3P of FIG. 5C, the flaps 3 of FIG. 10 are folded and the male touch fasteners 4 come into contact with, and engage with, the female touch fastener 5.

At this point, as the sub-holding surfaces 12s squarely oppose the main holding surface 11s, the touch fasteners 4 and 5 engage with each other while squarely opposing each other, thus making the engagement between the touch fasteners 4 and 5 reliable.

Thus, the flaps 3 of the diaper 1 of FIG. 1C are folded and the folded flaps 3 are fixed to the diaper body 2 via the male touch fasteners 4 and the female touch fastener 5, thereby making it possible to hold the flaps 3 in a folded state.

The folded state may be maintained through the angle θ3 about the main rotation shaft 91 of FIG. 2. Then, in the angle θ4, the closed arms 13 and the closed wrists 14 rotate in the opening direction.

Note that through the angle θ4, the diameter of the cam groove 17 gradually increases as it extends downstream Y1.

Before the arms 13 and the wrists 14 start opening, suction through the air holes h2 provided in the sub-holding surfaces 12s of FIG. 6A is discontinued.

After the arms 13 and the wrists 14 are opened, the diaper 1 is handed over to the conveyer device (not shown) at the hand-over position 4P of FIG. 2. In this hand-over process, suction through the air holes h1 provided in the main pad 11 of FIG. 6A is discontinued.

Note that the folding unit 10 which has handed over the diaper 1 continues to rotate toward the pickup position 1P.

[Embodiment 2]

FIGS. 9A to 11B show Embodiment 2. Embodiment 2 will now be described.

Figure 9A:
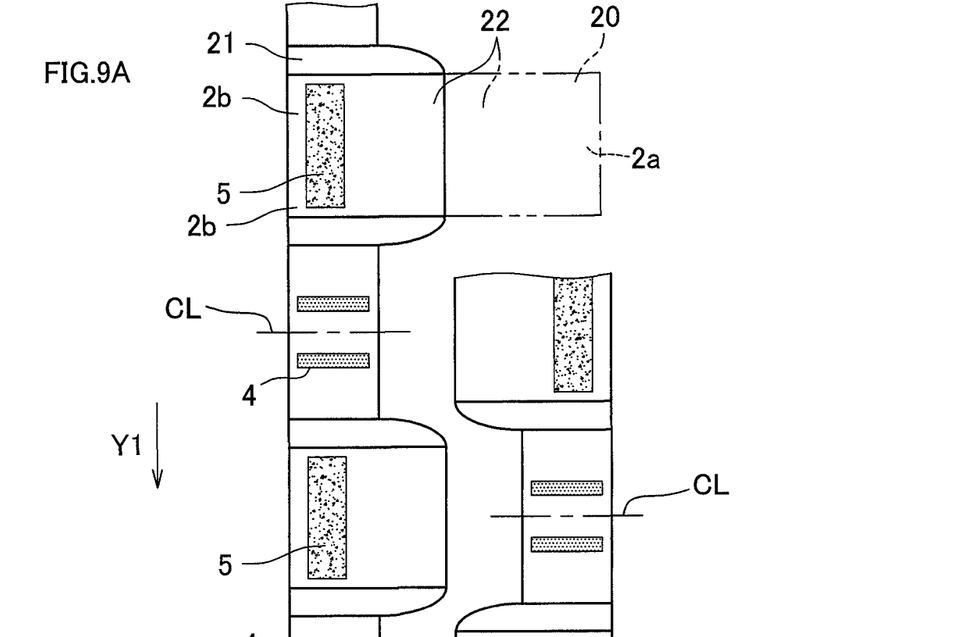
FIGS. 9A, 9B and 9C are schematic plan views each showing an arrangement in a case where diapers are arranged in two rows.
Figure 9B:
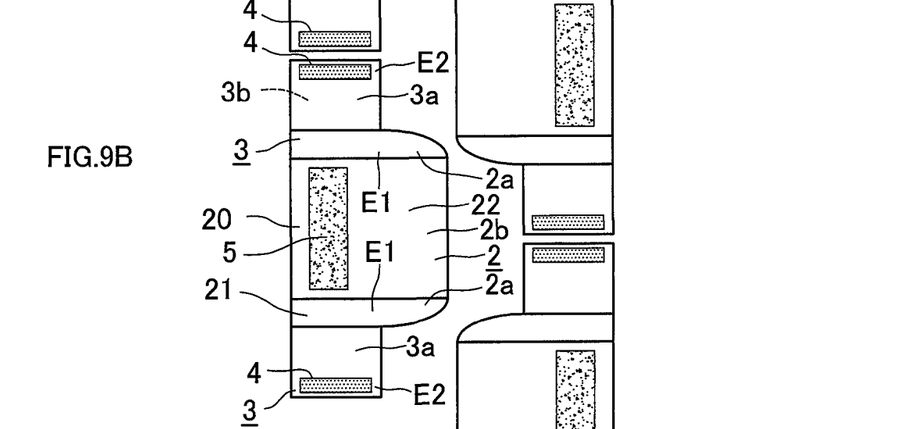
Figure 9C:
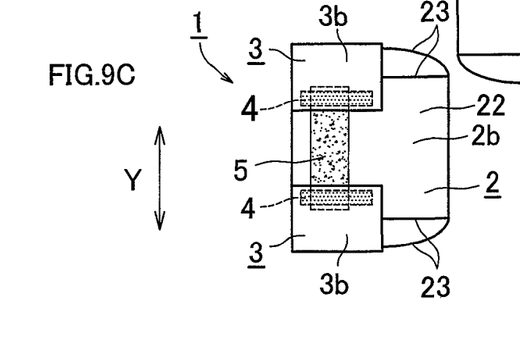

In Embodiment 2, a single folding drum is used to sever two strips of laminated web W shown in FIG. 9A into individual diapers 1 and folding the flaps 3.

As shown in FIG. 10, in the present embodiment, two rows of folding units 10 are arranged in a staggered pattern. With the present embodiment, the anvil 31 of a folding unit 10 of one row protrudes into between folding units 10 and 10 of the other row.

Figure 11A:
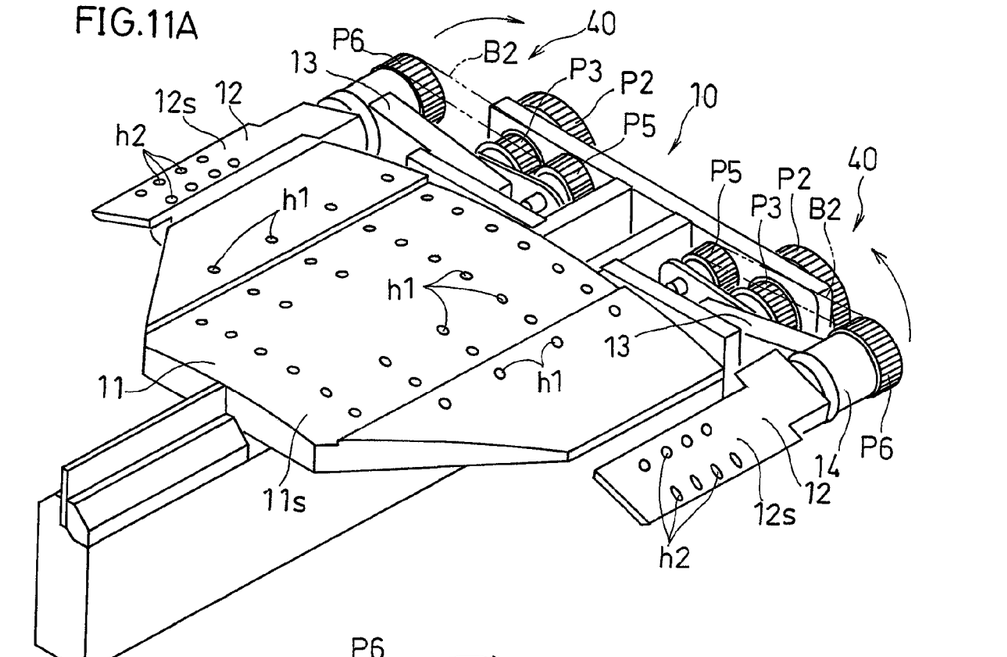
FIGS. 11A and 11B are schematic perspective views each showing a structure of a main pad, side pads and an anvil of the folding system.
Figure 11B:
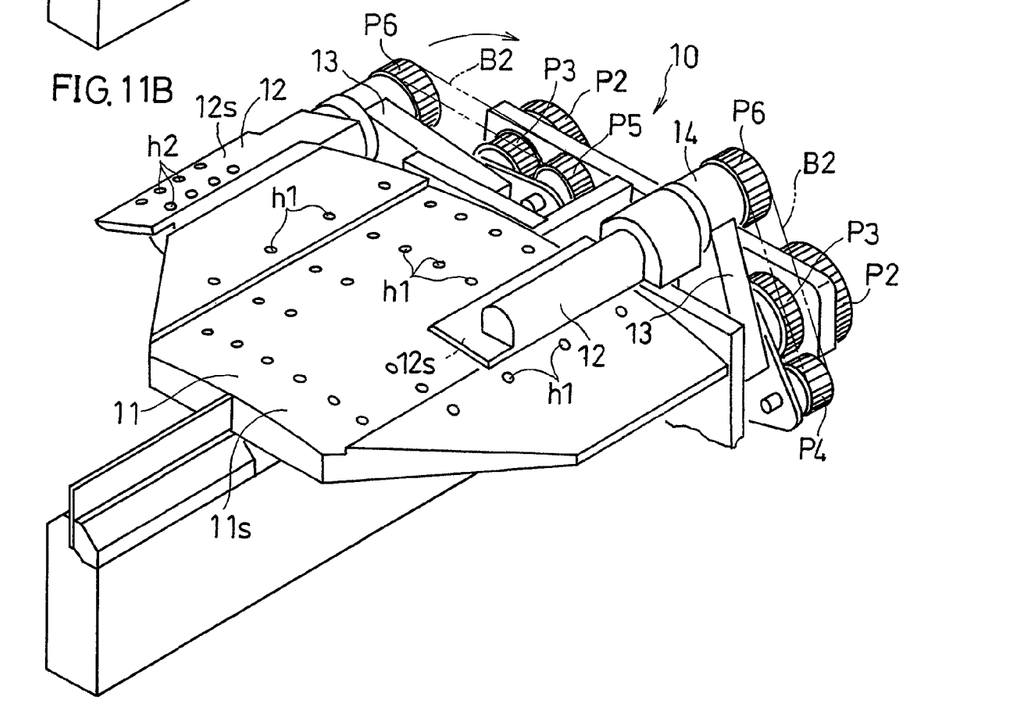

That is, in Embodiment 1 of FIG. 3, the anvil 31 of a folding unit 10 of one row is placed between folding units 10 and 10 of the same row. In contrast, in Embodiment 2, the anvil 31 of a folding unit 10 of one row protrudes toward the other row as shown in FIGS. 11A and 11B.

While preferred embodiments have been described above with reference to the drawings, obvious variations and modifications will readily occur to those skilled in the art upon reading the present specification.

For example, a flap may extend out in the girth direction from an edge of the front portion. The first and second fastener members may be absent, and the flaps may be tentatively fastened to the main body by a hot-melt adhesive.

Pads do not need to be sucked by a negative pressure, but a web may be held on pads by piercing a plurality of needles through the web.

The mechanism for rotating the arms and the wrists may be gears instead of belts. Mechanisms for rotating the arms and the wrists may be provided separately from each other.

It is not necessary to rotate both the arms and the wrists as long as the side pads are rotated so that the sub-holding surfaces oppose the main holding surface.

Thus, such variations and modifications shall fall within the scope of the present invention as defined by the appended claims.

INDUSTRIAL APPLICABILITY

The present invention is applicable to folding systems for folding flaps of worn articles such as disposable diapers.

DESCRIPTION OF THE REFERENCE NUMERALS

1: Diaper (an example of a disposable worn article)
2: Diaper body
2a: Skin-contact surface
2b: Non-skin-contact surface
3: Flap
3a: Skin-contact surface
3b: Non-skin-contact surface
4: Male touch fastener
5: Female touch fastener
9: Folding drum
91: Main rotation shaft
10: Folding unit 11: Main pad
11s: Main holding surface
12: Side pad
12s: Sub-holding surface
13: Arm
14: Wrist
15: Fixed frame
16: Rotating frame
17: Cam groove
18: Cam follower
20: Front portion
21: Back portion
22: Crotch portion
E1: Edge portion
E2: End portion
L1: First axis
L2: Second axis
L3: Normal
30: Severing device
31: Anvil
32: Cutter roller
33: Blade
40: Folding mechanism
41: Driving mechanism
42: Arm rotating mechanism
43: Wrist rotating mechanism
45: Arm rotation shaft
50: Pressing mechanism
Y: Girth direction
Y1: Downstream

The invention claimed is:

1. A flap folding system for a disposable article to be worn, being a device for folding a flap of a worn article having: a main body including a back portion covering a rear torso of a wearer, a crotch portion covering a crotch of the wearer, and a front portion covering a front torso of the wearer; and a flap extending in a girth direction from an edge portion of one of the back portion and the front portion of the main body to be fastened to the other one of the back portion and the front portion, the folding system comprising:

a main rotation shaft;

a plurality of main pads each for receiving at least the main body on a main holding surface thereof provided along a conveyance circle about the main rotation shaft and moving along the conveyance circle following rotation of the main rotation shaft while holding the main body on the main holding surface;

a pair of side pads provided for each of the main pads adjacent to each of the main pads on the conveyance circle for receiving at least an end portion of the flap in the girth direction on sub-holding surfaces thereof provided along the conveyance circle and holding the end portion of the flap on the sub-holding surfaces; and a folding mechanism for rotating the pair of side pads with respect to each of the main pads so that the sub-holding surfaces of the pair of side pads oppose the main holding surface of each of the main pads, thereby folding the flap, wherein the folding mechanism rotates the pair of side pads with respect to each of the main pads to a position such that the sub-holding surfaces oppose the main holding surface and the sub-holding surfaces are parallel to the main holding surface, and the folding mechanism comprises:

arms rotating about a pair of first axes parallel to the main rotation shaft;

wrists rotatably supporting the side pads about a pair of second axes parallel to the first axes at tips of the arms; and a driving mechanism for rotating the arms and the wrists in a predetermined rotation direction so as to fold the flap.

2. The flap folding system for a disposable article to be worn according to claim 1, the driving mechanism comprising:

an arm rotating mechanism for rotating the arms about the first axes so that the pair of side pads move from a first position adjacent to each of the main pads to a second position on an outer circumferential side of each of the main pads as the main pads rotate along the conveyance circle following the rotation of the main rotation shaft; and a wrist rotating mechanism for rotating the side pads about the second axes at the wrists following the rotation of the arms by the arm rotating mechanism.

3. The flap folding system for a disposable article to be worn according to claim 1, wherein the main pads and the side pads pick up a laminated web to be the worn article at a pickup position upstream of a folding position where the folding is done, and the main pads hand over the laminated web to a conveyer device downstream at a hand-over position downstream of the folding position.

4. The flap folding system for a disposable article to be worn according to claim 3, further comprising a severing device for severing the laminated web being stretched along the conveyance circle by each of the main pads and the side pads at a severing position between the pickup position and the folding position.

5. The flap folding system for a disposable article to be worn according to claim 1, wherein the holding of the main body by each of the main pads is done at least in an area of each of the main pads where the pair of side pads opposes each of the main pads.

6. The flap folding system for a disposable article to be worn according to claim 1, wherein a first fastener member is provided on a skin-contact surface side of the flap to be folded, and a second fastener member is provided on the main body on which the folded flap lies so as to engage with the first fastener member.

7. The flap folding system for a disposable article to be worn according to claim 1, wherein the main pads, the pairs of side pads and the folding mechanisms are arranged in two rows along the conveyance circle, with the main pads of the two rows arranged in a staggered pattern with each other.

* * * * *